(12) United States Patent
Chang

(10) Patent No.: US 7,683,331 B2
(45) Date of Patent: Mar. 23, 2010

(54) SINGLE PHOTON EMISSION COMPUTED TOMOGRAPHY (SPECT) SYSTEM FOR CARDIAC IMAGING

(75) Inventor: Wei Chang, Lisle, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 11/999,901

(22) Filed: Dec. 7, 2007

(65) Prior Publication Data
US 2008/0135768 A1 Jun. 12, 2008

Related U.S. Application Data

(60) Provisional application No. 60/869,274, filed on Dec. 8, 2006.

(51) Int. Cl.
*G01T 1/166* (2006.01)
(52) U.S. Cl. .................................. 250/363.04
(58) Field of Classification Search . 250/363.01–363.1, 250/370.01–370.15; 378/98.8
See application file for complete search history.

(56) References Cited

U.S. PATENT DOCUMENTS

| 5,523,571 | A * | 6/1996 | Velazquez et al. ...... 250/363.05 |
| 6,949,748 | B2 * | 9/2005 | Ziock et al. ............ 250/370.01 |
| 7,026,623 | B2 | 4/2006 | Oaknin et al. |
| 2004/0251419 | A1 * | 12/2004 | Nelson et al. .......... 250/370.09 |
| 2005/0001170 | A1 | 1/2005 | Juni |
| 2006/0173302 | A1 * | 8/2006 | Conwell ..................... 600/436 |

OTHER PUBLICATIONS

Bal et al. "Evaluating rotating slant-hole SPECT with respect to parallel hole SPECT,", 2001, IEEE, Nuclear Science Symposium, vol. 3, pp. 22/67-22/71.*
Hoppin et al., "Evaluating estimation techniques in medical imaging without a gold standard: Experimental Validation," 2003, The Proceedings of SPIE, vol. 5034, pp. 230-237.*
W. Chang et al., "A Cylindrical Geometry for Cardiac SPECT Imaging", IEEE Transaction on Nuclear Science, Aug. 1996, vol. 43, No. 4, pp. 2219-2224.
Rogers, W.L. et al., "SPRINT II: A Second Generation Single Photon Ring Tomograph, IEEE Transaction on Medical Imaging", Dec. 1988, vol. 7, No. 4, pp. 291-297.

* cited by examiner

*Primary Examiner*—David P Porta
*Assistant Examiner*—Kiho Kim
(74) *Attorney, Agent, or Firm*—Iandiorio Teska & Coleman

(57) ABSTRACT

A single photon emission computed tomography (SPECT) system for cardiac imaging including an open arc-shaped frame. A collimator subsystem is shaped to approximately match the thoracic contour to optimize the geometric efficiency for detecting photons emitted from the heart of patients having different sizes and weights and shaped to surround and position the collimator subsystem closely proximate a heart of a patient of the patients encompassed by at least one predetermined image volume for optimizing collimation of radiation photons emitted from the heart. The collimator subsystem is facilitated by a tracking system that is capable of quickly bringing up the collimator component, which meets a specific set of collimation requirements, into place for imaging. And an open arc-shaped detector system is coupled to the collimator subsystem having a shape closely matching the shape of the collimator subsystem for detecting collimated radiation photons from the collimator subsystem and generating output electrical signals.

27 Claims, 12 Drawing Sheets

US 7,683,331 B2

SINGLE PHOTON EMISSION COMPUTED TOMOGRAPHY (SPECT) SYSTEM FOR CARDIAC IMAGING

RELATED APPLICATIONS

This application claims the benefit of U.S. Provisional Application No. 60/869,274, filed Dec. 8, 2006, which is incorporated by reference herein.

FIELD OF THE INVENTION

This subject invention relates to an improved single photon emission computed tomography (SPECT) system for cardiac imaging.

BACKGROUND OF THE INVENTION

SPECT systems are often used to show the distribution of a radioactive substance inside a patient's body. A source of penetrating radiation is administered to the patient, which typically consists of a pharmaceutical tagged with a radionuclide which emits radiation photons (radiopharmaceutical). The radiopharmaceutical is designed to be absorbed in a target organ, such as the heart muscle, or other organs or body part of interest. The emitted radiation photons are collimated with a collimator subsystem and detected by a detector subsystem which generates output electrical signals which are digitized and processed by a computer system to generate images of the regional distribution of the radioactive sources in and around the target organ.

One prior SPECT system proposed by the inventor hereof utilizes a large circular shape design for the frame, or the gantry, collimator subsystem, and the detector subsystem which attempted to accommodate a large patient cross-section while placing the patient's heart at the geometric center for imaging from multiple directions simultaneously. However, because of the off-center location of heart, the circular geometry had to be fairly large to enclose a large patient's thorax. As a result, the long-distance collimation offsets the potential gain in geometric efficiency and renders the circular design less than optimum. Furthermore, the design devoted considerable collimator and detector area to the patient's right-posterior side, where the heart is too distant from the collimator for effective collimation. The typical problem of low photon sensitivity in SPECT is further compounded in cardiac imaging where the desirable radiation photons are scarce: only about 2-4% of the injected dose is absorbed in the myocardium of the heart. This circular design approach results in a limited return of the heavily attenuated and scattered photons and sub-optimal image quality.

Conventional and contemporary SPECT systems used and proposed for cardiac imaging suffer from a major weakness: these systems do not provide optimum detection coverage for photons emitted from the heart because they allow a large fraction of high quality photons to escape detection. This is well demonstrated by the requirement of using detector rotation around the patient, e.g., as utilized in conventional dual-head systems. Obviously, as detector rotates in incremental steps to catch photons on the far side of the patient, the photons on the near side escape coverage. Additionally, the detector area of prior systems has not been used efficiently for detection of photons emitted from the heart: most of the time, a large portion of the detector area is directed to the surrounding background area of the thorax.

Thus, an optimal system design for cardiac SPECT imaging needs to provide efficient and optimum detector coverage for high quality photons emitted from the heart, while effective collimation and adequate data sampling are achieved at the same time. Therefore, how to obtain an optimal balance between detector coverage, collimation, and sampling is the key to the design of a high-performance SPECT system.

The collimator subsystems of conventional SPECT systems are designed with only one predefined set of collimation parameters. For different imaging requirements, or for patient having different sizes, a different set of collimation parameters is often preferred. Therefore a different collimator with different collimation parameters is needed. However, changing the collimator during a conventional SPECT imaging procedure is not realistically feasible because such a procedure takes an inordinate amount of time and effort, and more importantly, it disturbs the patient's imaging position which is hard to be restored after the collimator change. The result is that conventional SPECT systems are not flexible in accommodating different collimation requirements to suit various clinical situations and patients having different sizes.

Additionally, conventional SPECT systems typically incrementally rotate the large, heavy collimator and the detector subsystem about the patient to obtain a plurality of projection images (projections). Each time the collimator and the detector subsystem are rotated step-by-step, the collimator and detector follow the patient's body contour by successively adjusting their radial and lateral positions. Such a technique is cumbersome, not easily reproducible, prone to both mechanical and electrical errors, slow, inefficient, utilizes expensive hardware to rotate large heavy collimator and detector subsystems, and requires extensive safety measures to protect the patient. As a result, conventional SPECT images have large variations in image quality and reproducibility, which make comparison of images from different facilities or from different times at the same facility difficult.

BRIEF SUMMARY OF THE INVENTION

It is therefore an object of this invention to provide an improved SPECT system for cardiac imaging.

It is a further object of this invention to provide such a SPECT system for cardiac imaging in which the shape and size of the collimator and detector subsystems optimize detection of radiation photons emitted from the heart.

It is a further object of this invention to provide such a SPECT system for cardiac imaging which provides a plurality of predetermined imaging volumes of various sizes and locations for optimizing data acquisition and image quality.

It is a further object of this invention to provide such a SPECT system for cardiac imaging which provides high quality SPECT images for patients having different sizes and shapes in a typical patient population.

It is a further object of this invention to provide such a SPECT system for cardiac imaging which positions a heart to a desired location based on a previous scout image to optimize SPECT imaging.

It is a further object of this invention to provide such a SPECT system for cardiac imaging which provides a plurality of collimation parameters.

It is a further object of this invention to provide such a SPECT system for cardiac imaging which eliminates the problems associated with moving a collimator and a detector subsystem about a patient.

It is a further object of this invention to provide such a SPECT system for cardiac imaging which is easier to use.

It is a further object of this invention to provide such a SPECT system for cardiac imaging which provides images that are reproducible at different facilities.

It is a further object of this invention to provide such a SPECT system for cardiac imaging which provides images that are reproducible at different times at the same facility.

It is a further object of this invention to provide such a SPECT system for cardiac imaging which is cost effective relative to the performance it can achieve.

It is a further object of this invention to provide such a SPECT system for cardiac imaging which improves sensitivity for a given imaging spatial resolution.

It is a further object of this invention to provide such a SPECT system for cardiac imaging which improves imaging spatial resolution for a given sensitivity.

The subject invention, however, in other embodiments, need not achieve all these objectives and the claims hereof should not be limited to structures or methods capable of achieving these objectives.

This invention features a single photon emission computed tomography (SPECT) system for cardiac imaging including an open arc-shaped frame. A collimator subsystem having an open arc-shape is shaped to approximately match the thoracic contour of patients having different sizes and weights and shaped to surround and position the collimator subsystem closely proximate a heart of a patient of the patients encompassed by at least one predetermined image volume for optimizing collimation of radiation photons emitted from the heart. An open arc-shaped detector system is coupled to the collimator subsystem having a shape closely matching the shape of the collimator subsystem for detecting collimated radiation photons from the collimator subsystem and generating output electrical signals.

In another embodiment, the shape of the collimator subsystem and the detector subsystems may optimize collimation and detection of the radiation photons for a majority of the patients of a patient population. The predetermined imaging volume may include a three-dimensional cylindrical imaging volume. The arc-shaped frame, the collimator system, and the detector subsystem may be subtended at an angle in the range of about 180° to 220° with respect to the center of the predetermined imaging volume. The collimator subsystem may include a slit-plate comprising a predetermined number of spaced longitudinal slits each having a predetermined width for transversely collimating the radiation photons. The predetermined width of each of the plurality of spaced longitudinal slits may be configured to adjust spatial resolution of transverse collimation. The system may further include a plurality of slit-guides attached proximate each side of each of the plurality of longitudinal slits. The angle of the slit-guides and the location of the spaced longitudinal slits may be configured to provide a plurality of non-overlapping projections that define the size and location of the at least one predetermined imaging volume. The size and location of the at least one predetermined image volume and the plurality of non-overlapping projections may provide high geometric efficiency in the detection of radiation photons emitted from the heart. The at least one predetermined image volume may be configured for patients having different thoracic contours and/or different sized hearts and/or different locations of the heart relative to a predefined central axis. The at least one predetermined imaging volume may include a large three-dimensional imaging volume for generating a scout image which estimates a three-dimensional center and the general size of the heart. The at least one predetermined imaging volume may include a small three-dimensional imaging volume for generating SPECT images of the heart. The combination of the location of spaced longitudinal slits, the angle of the slit-guides, and the distance between the slit plate and the detector subsystem may be adjusted for minification of a plurality of simultaneous non-overlapping projections such that a maximum number of projections can be cast on the detection system to provide high geometric efficiency for generating one or more SPECT images. The one or more SPECT images may be obtained by using image reconstruction of the plurality of simultaneous non-overlapping projections. The collimator subsystem may include a plurality of transversely spaced slats disposed behind the slit-plate for longitudinally collimating the radiation photons. The location of each of the plurality of transversely spaced slats may be configured to adjust spatial resolution of longitudinal collimation. The transversely spaced slats may be configured to converge on predetermined focal points to accommodate cone-beams of radiation photons emitted from the heart for increasing the number of radiation photons detected by the detector subsystem. The slit-plate may be configured as a flexible loop moveably coupled to the frame having a plurality of sections each configured to provide a unique predetermined imaging volume having a predetermined size and location, and a spatial resolution. A desired section of the flexible loop may be positioned proximate and surrounding the at least one predetermined imaging volume of the patient by driving the flexible loop to a predetermined location on the collimator subsystem. The system may further include a plurality of connected flexible loops moveably coupled to the frame, each loop including a plurality of sections configured to provide a unique predetermined imaging volume of a predetermined size, location, and spatial resolution. The system may further include a patient positioning subsystem for positioning the patient such that the heart is located proximate the center of the predetermined imaging volume based on previous scout images of the heart. The patient positioning subsystem may incrementally rotate the patient about a central longitudinal axis of the at least one predetermined imaging volume for obtaining a plurality of additional projection images. The patient positioning subsystem may intermittently and incrementally rotate the patient about a predefined central longitudinal axis of a small predetermined three-dimensional imaging volume for obtaining a plurality of sequentially acquired sets of simultaneous projections and reconstructing one or more SPECT images. A patient positioning subsystem may position the predefined imaging volume encompassing the heart up and down about a longitudinal axis for acquiring additional cone-beam data set in a longitudinal plane. The open arc-shaped frame may have a shape closely matching the shape of the collimator subsystem.

This invention further features a single photon emission computed tomography (SPECT) system for cardiac imaging including an open arc-shaped frame. A collimator subsystem is shaped to approximately match the thoracic contour of patients having different sizes and weights and shaped to surround and position the collimator subsystem closely proximate a heart of a patient of the patients encompassed by at least one predetermined image volume for optimizing collimation of radiation photons emitted from the heart. An open arc-shaped detector system is coupled to the collimator subsystem having a shape closely matching the shape of the collimator subsystem for detecting collimated radiation photons from the collimator subsystem and generating output electrical signals. A patient positioning subsystem positions the patient such that the heart is located proximate the center of the predetermined imaging volume configured to optimize SPECT imaging based on previous scout images of the heart.

This invention also features a single photon emission computed tomography (SPECT) system for cardiac-imaging including an open arc-shaped frame. A collimator subsystem is shaped to approximately match the thoracic contour of patients having different sizes and weights and shaped to surround and position the collimator subsystem closely proximate a heart of a patient of the patients encompassed by at least one predetermined image volume for optimizing collimation of radiation photons emitted from the heart. The collimator system further includes a slit-plate configured as a flexible loop moveably coupled to the frame having a plurality of sections each configured to provide a unique predetermined imaging volume having a predetermined size and location, and a spatial resolution. An open arc-shaped detector system is coupled to the collimator subsystem having a shape closely matching the shape of the collimator subsystem for detecting collimated radiation photons from the collimator subsystem and generating output electrical signals.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
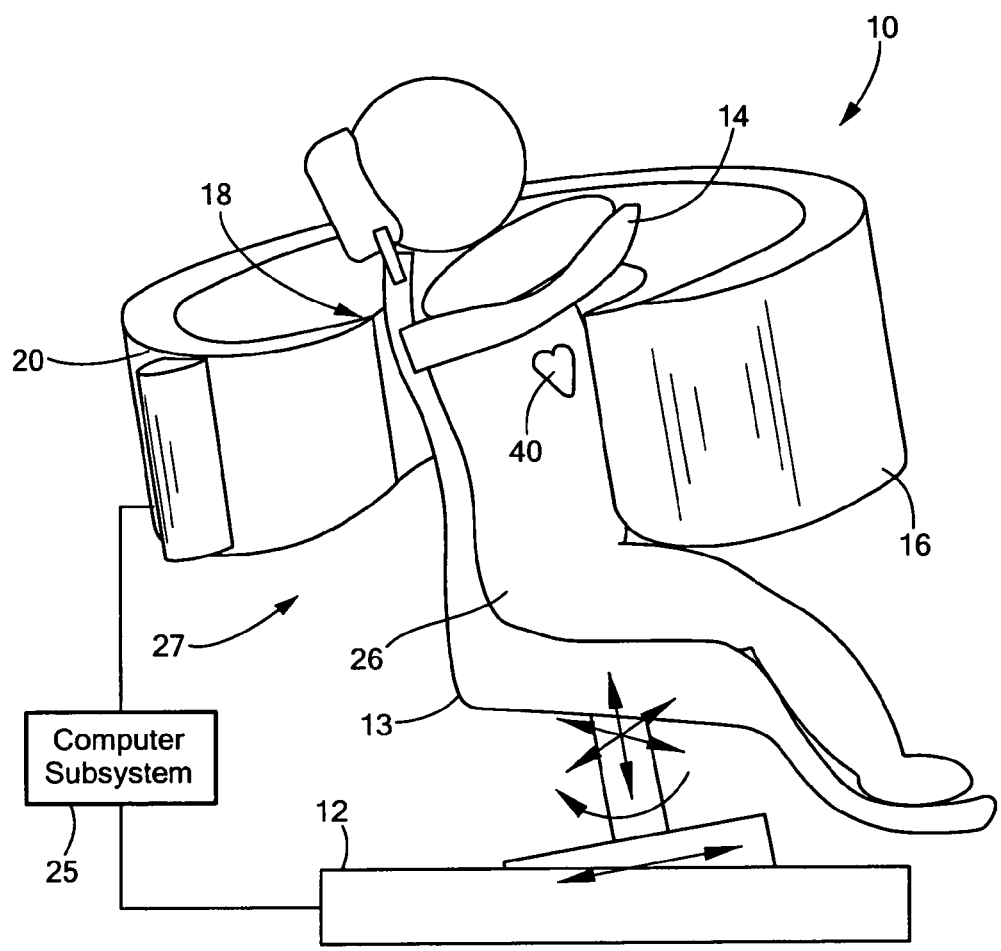
FIG. 1 is a three-dimensional side view of one embodiment of the SPECT system for cardiac imaging of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
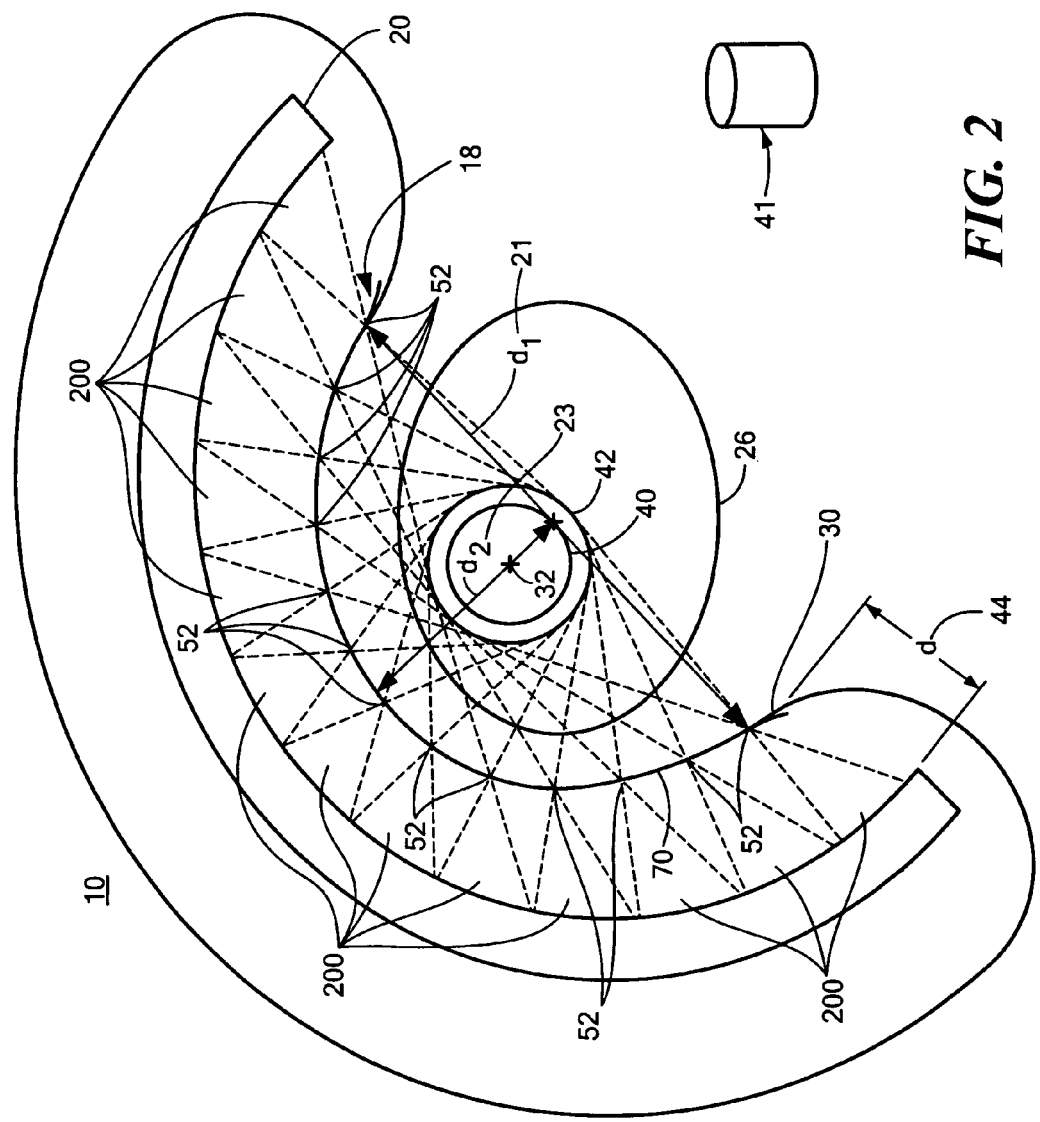
FIG. 2 is a schematic top view of one embodiment of the SPECT system for cardiac imaging of this invention configured for a predetermined imaging volume (PIV) of a typical sized patient.
Figure 3:
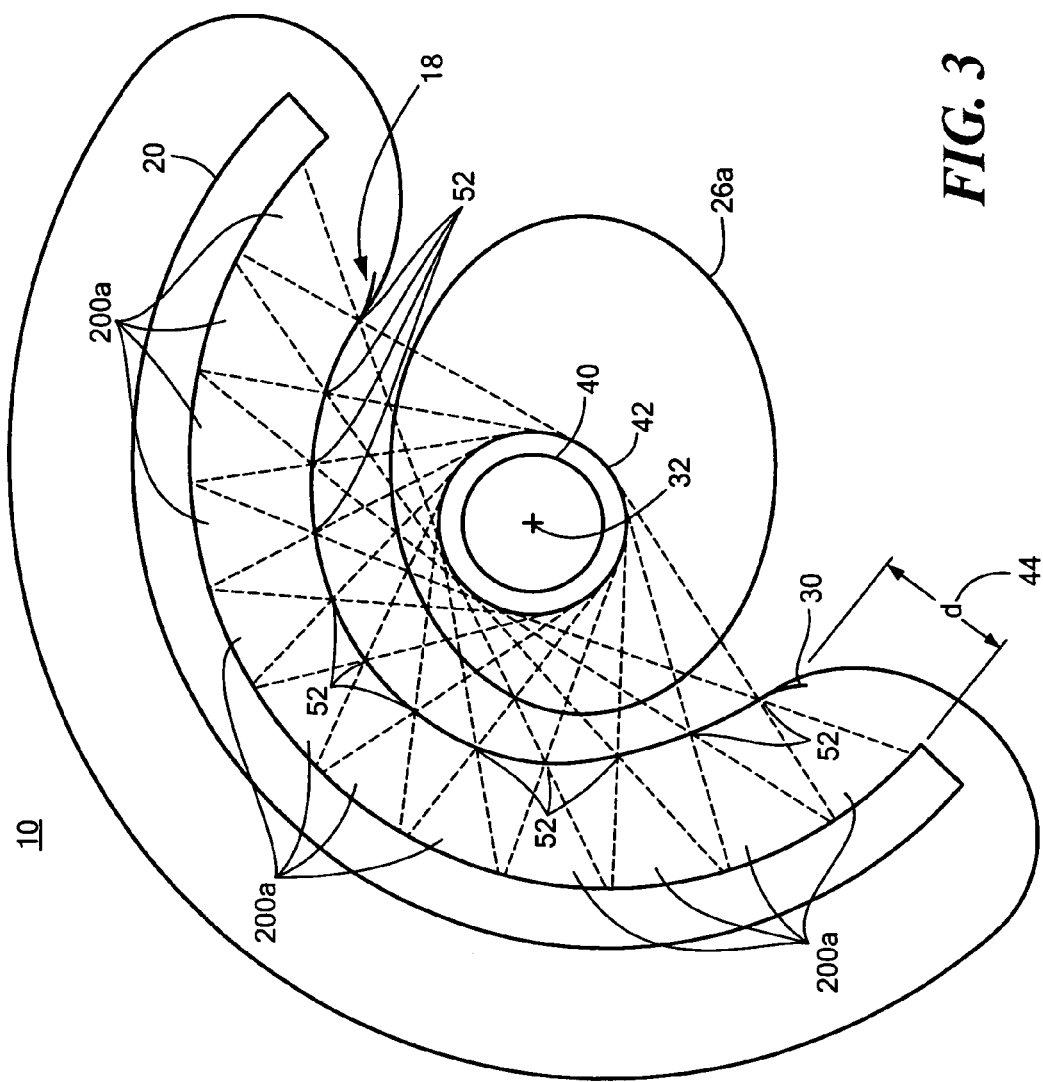
FIG. 3 is a schematic top view one embodiment of the SPECT system for cardiac imaging of this invention configured for PIV of a large patient.

There is shown in FIG. 1, one embodiment of SPECT system 10 of this invention. System 10 includes collimator subsystem 18 coupled to frame 16, which is shaped to an open-arc to approximately match the thoracic contour of patient 26, as better shown, e.g., in FIGS. 2 and 3. Collimator subsystem 18, FIGS. 1-3 is fairly large and has a cross-section, e.g., about 55 cm as shown at $d_1$-21, FIG. 2, and about 25 cm as shown at $d_2$-23, or any equivalent dimensions as known by those skilled in the art. Collimator subsystem 18, FIGS. 2-3, is responsive to radiation photons emitted from heart 40, e.g., the circle representing the heart of patient 26 as shown in FIG. 1. As discussed in the Background section above, radiation photons emit from heart 40 as a result from intravenous injection of a radiopharmaceutical. The shape of collimator subsystem 18, FIGS. 1-3, is designed to approximately the thoracic contour of patient 26. This allows collimator subsystem 18 to be closely proximate to heart 40 to optimize collimation of radiation photons from heart 40 encompassed by at least one PIV, e.g., PIV 42, FIG. 2, of a typical sized patient 26, or PIV 42a, FIG. 3, of a larger sized patient. The shape of open-arc collimator subsystem 18, FIGS. 1-3 is also designed to accommodate data sampling for the off-center location of heart 40. The result is collimator subsystem 18 effectively collimates radiation photons from heart 40 of the majority of the patients in a typical patient population. Collimator subsystem 18 may be oval shaped, elliptical shaped, hyperbolic shaped, or a composite (of any of the aforementioned shapes), or any shape known to those skilled in the art which will result in collimator subsystem 18 approximately matching the thoracic contour of patient 26 and being located closely proximate heart 40 encompassed by PIV 42, FIG. 2, or PIV 42a, FIG. 3.

Detector subsystem 20, FIGS. 2 and 3, is located behind collimator subsystem and has a shape which closely matches the shape of collimator subsystem 18, as discussed above. Detector subsystem 20 is responsive to collimator subsystem 18 and detects collimated radiation photons emitted by heart 40 and generates output electrical signals. Detector subsystem 20 preferably includes a plurality of closely spaced detector modules 72, FIGS. 4 and 5 that maximize packing fraction and detection efficiency while providing high intrinsic spatial resolution (ISR). Detector modules 72 could be made from a variety of radiation detector material, such as scintillation detectors or room-temperature solid-state detectors. Detector modules 72 may be solid-state CZT detectors or advanced pixellated scintillation detectors, as known by those skilled in the art. Computer system 25, FIG. 1, receives digitized output electrical signals from the plurality of detectors and its associated electronics processing subsystem and generates one or more raw projection images of the heart.

Preferably arc-shaped frame 16, FIGS. 1-3, collimator subsystem 18, and detector subsystem 20 are subtended at an angle in the range of about 180° to 220° with respect to center 32 of heart 40.

Figure 4:
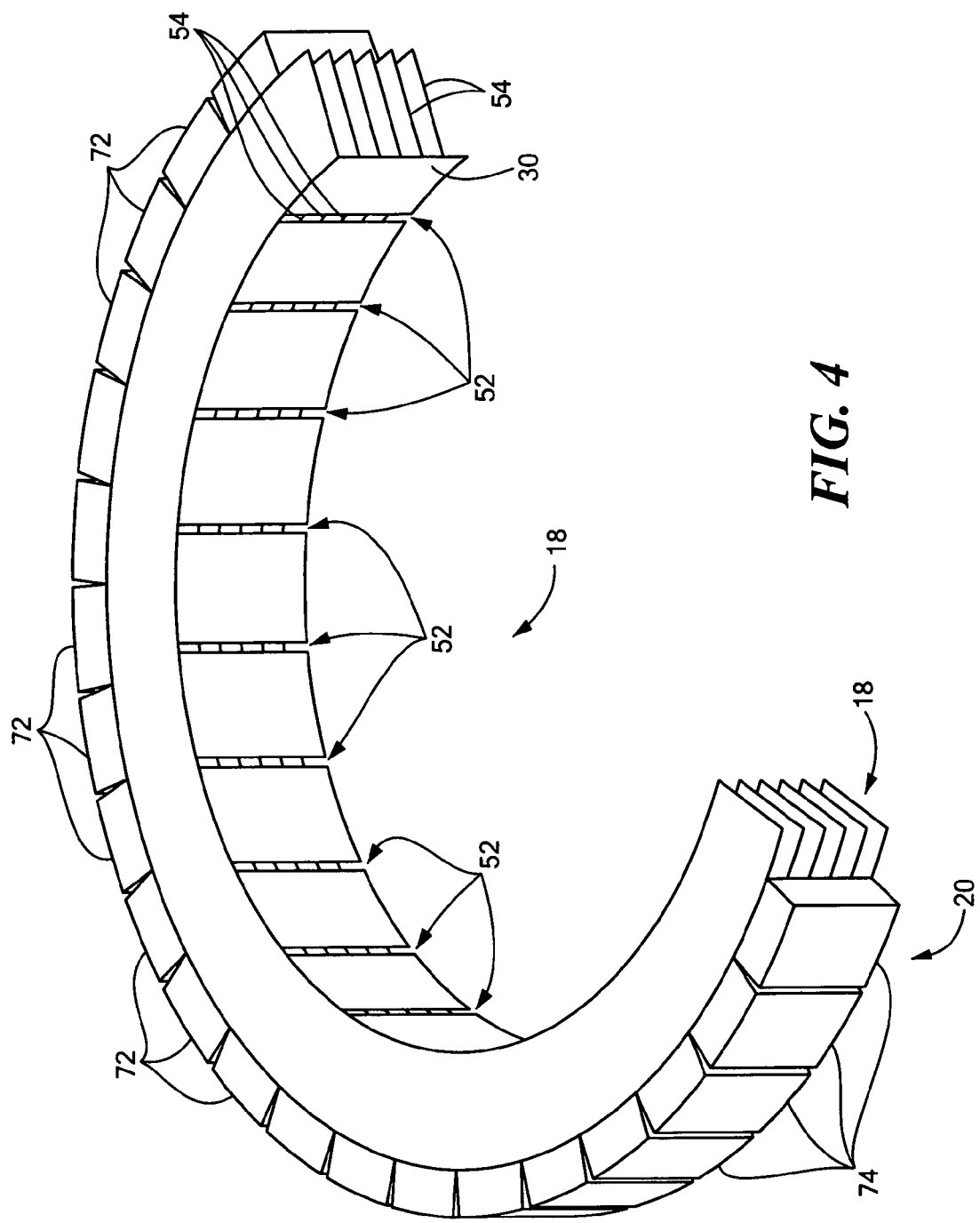
FIG. 4 is a three-dimensional view of a one embodiment of the collimator subsystem and the detector subsystem of this invention shown in FIGS. 1-3 used for high quality SPECT images of the heart.

In one design, collimator subsystem 18, FIGS. 2 and 3, includes slit-plate 30 having a predetermined number of spaced longitudinal slits 52 of a predetermined width. In this example, each slit 52 in slit-plate 30 has a predetermined width of about, e.g., 2 to 5 mm, as shown in FIG. 4. Slits 52 transversely collimate the radiation photons emitted from heart 40 encompassed by PIV 42, FIG. 2, or PIV 42a, FIG. 3. Each slit 52 functions as a 1D pinhole in the transverse plane casting a plurality of projections 200, FIG. 2, or a plurality of projections 200a, FIG. 3, of radiation photons emitted from PIV 42, or PIV 42a, respectively, onto detector subsystem 20.

Figure 5:
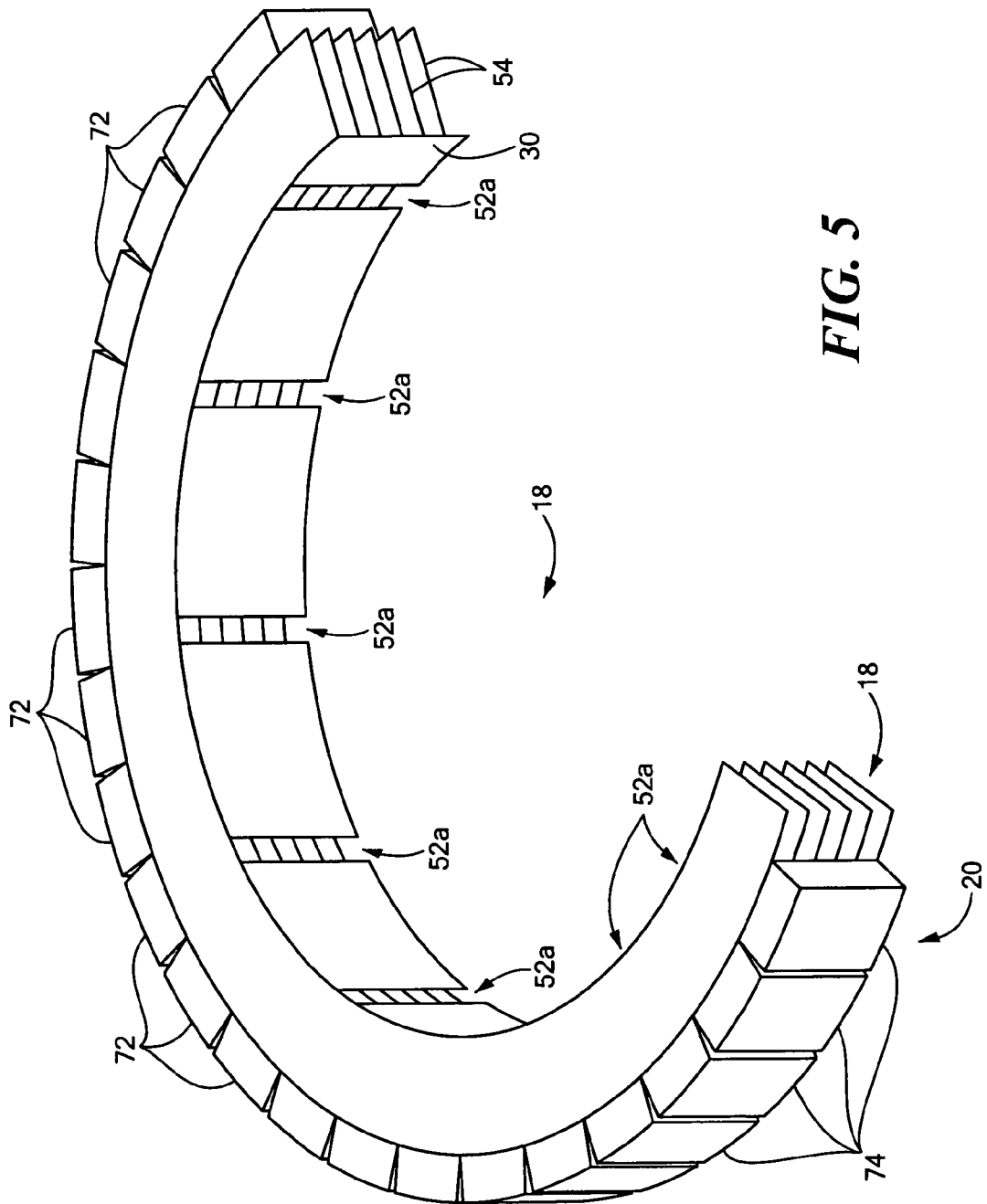
FIG. 5 is a three-dimensional view of another embodiment of the collimator subsystem and the detector subsystem of this invention shown in FIG. 1-3 used for obtaining scout images.

In another design, collimator subsystem 18, FIG. 5, includes a predetermined number of spaced wider slits 52a, e.g., about 5 to 8 slits 52a, having a predetermined wider width of about, e.g., about 8-12 mm.

The width of each of longitudinal slits 52, and slits 52a, FIGS. 2-5, is configured to adjust spatial resolution and photon sensitivity of transverse collimation of the radiation photons emitted from the heart 40. Wider slits, e.g., slits 52a, FIG. 5, provide generally lower spatial resolution but are more sensitive, e.g., for use with scout imaging. Narrower slits, e.g. slits 52, FIG. 2-4 provide generally higher spatial resolution but are less sensitive, e.g., for the construction of more accurate SPECT images of the PIV 42, FIG. 2 or PIV 42a, FIG. 3, with heart 40 therein.

Figure 6:
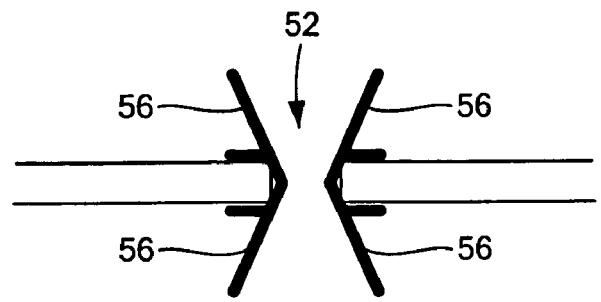
FIG. 6 is a schematic side view showing a one embodiment of slit-guides disposed on each side of the longitudinal slits shown in FIGS. 2-5.

In one preferred embodiment of this invention, collimator subsystem 18, FIGS. 1-5, includes slit-guides 56, FIG. 6, attached proximate each side of each of spaced longitudinal slits 52, 52a. In one example, slit-guides 56 are made of lead or similar type radiation-opaque material. The angle $\theta_1$-55, FIG. 7, of slit-guides 56, and the angle $\theta_2$-57, of slit-guides 56 with respect to axis 59 and the spacing between slits 52, 52a, FIGS. 2-5, are configured to define, inter alia, the size and location of PIV 42, FIG. 2, for a typical sized patient 26, PIV 42a, FIG. 3 for a larger patient 26, and a large PIV 42b, FIG. 8 for scout imaging. The combination of the angle of the slit-guides 56 and the spacing between slits 52, 52a provides the flexibility to define multiple PIVs at predetermined locations needed for patients having different thoracic contours, weights, and different sized hearts located further from central longitudinal axis 32 than a typical patient 26. The precisely targeted and optimized design and selection of PIVs 42, 42a, and 42b, results in high quality SPECT imaging and improved scout images.

Figure 7:
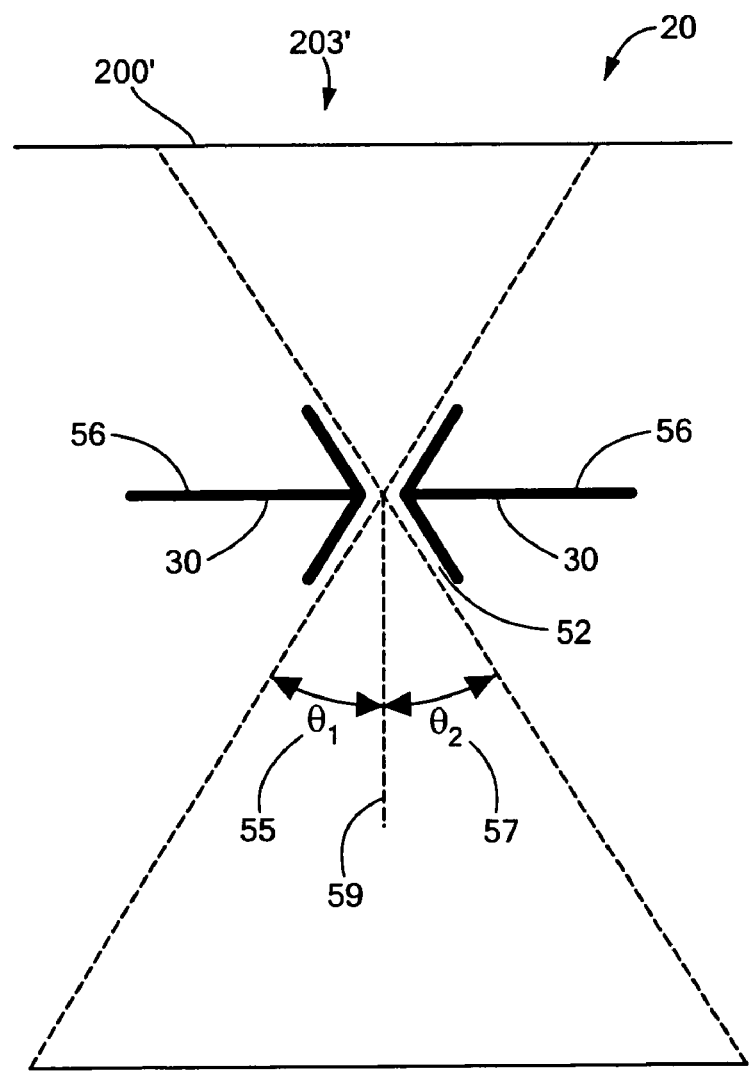
FIG. 7 is a schematic side view showing in further detail the angle of the slit-guide shown in FIG. 6.
Figure 8:
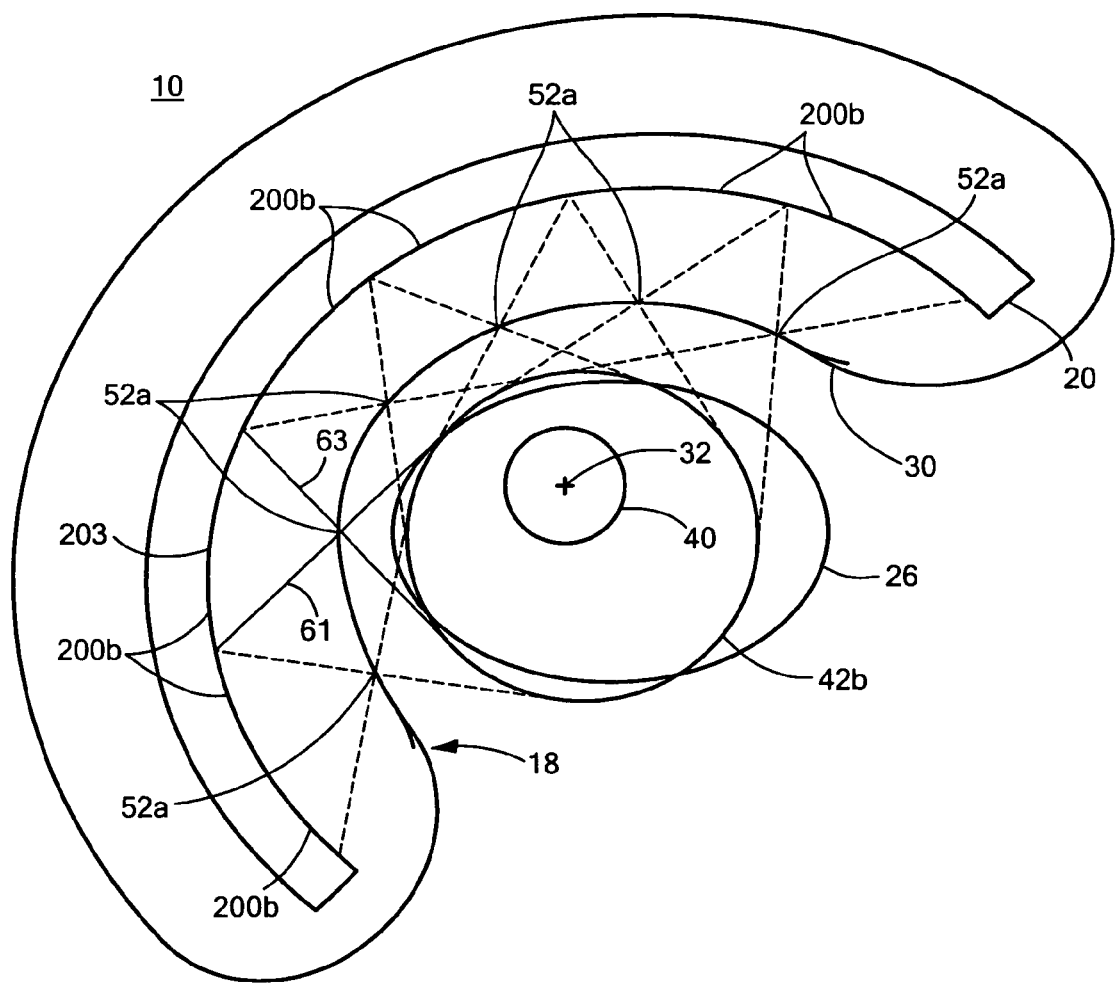
FIG. 8 is a schematic top view of another embodiment of the SPECT system for cardiac imaging of this invention configured for a large PIV used for scout imaging.
Figure 9:
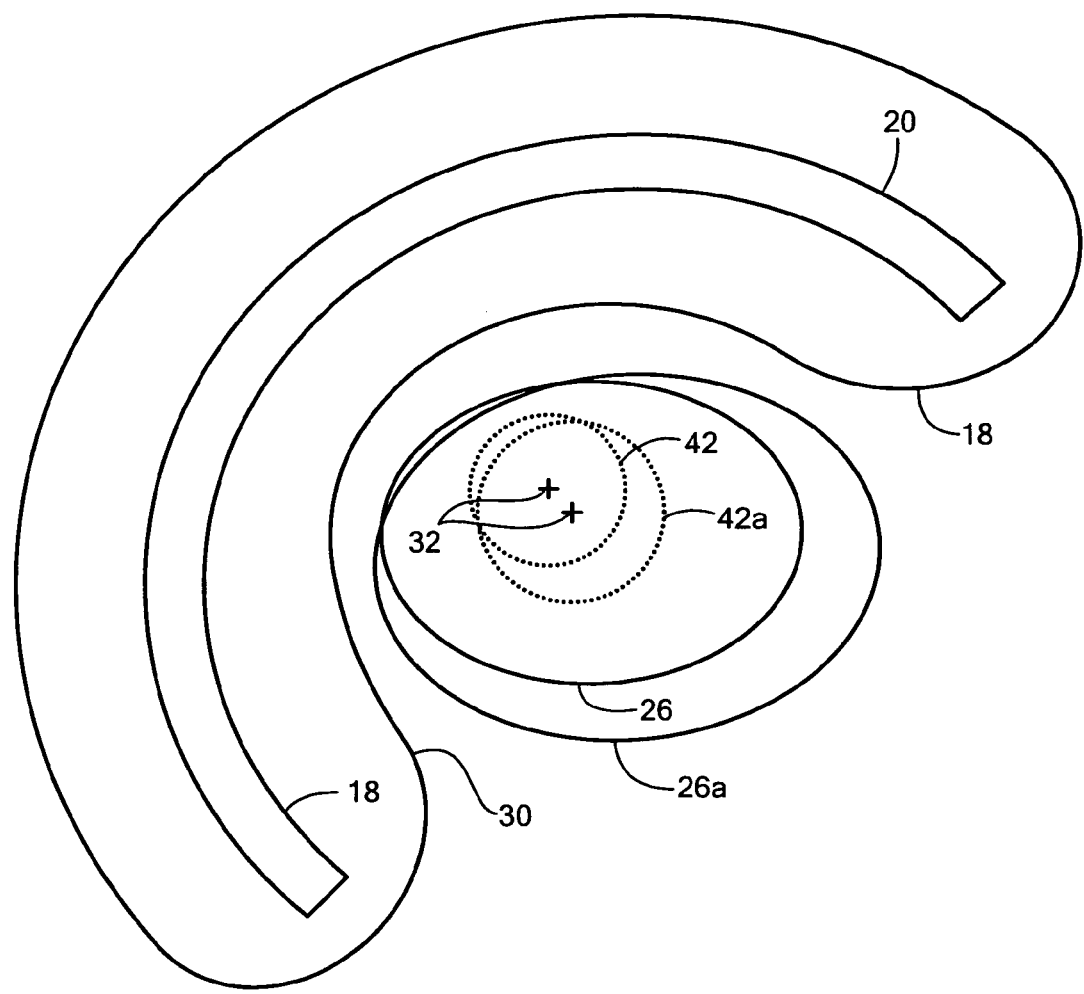
FIG. 9 is a schematic top view showing a comparison of the PIVs and patients shown in FIGS. 2 and 3.

For example, the angle $\theta_1$-55 and $\theta_2$-57, FIG. 7, with respect to axis 59, of slit-guides 56 and the spacing between slits 52, FIG. 2, defines a plurality of non-overlapping projections 200 which are cast on detector subsystem 20 to define PIV 42 for typical sized patient 26. Similarly, the combination of the angle $\theta_1$-55 and $\theta_2$-57, of the slit-guides 56, FIG. 7, and the spacing between slits 52, FIG. 3 defines a plurality of non-overlapping projections 200a, FIG. 3 which are cast on detector subsystem 20 to define PIV 42a of a larger sized patient 26a having a heart 40 which is larger and located further from central longitudinal axis 32 than a typical patient 26. FIG. 9, where like parts have been given like numbers, shows a comparison of PIV 42 of patient 26 and PIV 42a of larger patient 26a, as shown in FIGS. 2 and 3, respectively. Additionally, the combination of the angle $\theta_1$-55 and $\theta_2$-57 with respect of axis 59, FIG. 7, and the spacing between longitudinal slits 52a, FIG. 8, can also be configured to define a plurality of non-overlapping projections 200b which are cast on detector subsystem 20 to define a much larger PIV 42b, in the thoracic cross-section of patient 26 that covers heart 40 for generating a series of scout images to locate the center of heart 40. In this example, slit-plate 30 of collimator subsystem 18 may include about 5 to 8, e.g., 6 longitudinal slits 52a, as better shown in FIG. 5, each having a width of about 10 mm. Lines 61 and 63, FIG. 8, show two exemplary peripheral paths of radiation photons emitted from large PIV 42b and cast on detector subsystem 20 to create one of the plurality of projections 200b, indicated at 203. Center 32 and the longitudinal central axis that passes through center 32 of the heart 40 can be estimated either by inspecting raw projections of scout images or by real-time tomographic reconstruction of the plurality of raw projections 200b cast on the detector subsystem 20 to derive three-dimensional scout SPECT images. Thus, the wider width of the slits 52a provides quick, low-resolution images of the large PIV 42b for scout SPECT imaging.

The result is SPECT system 10 for cardiac imaging of this invention provides multiple PIVs at multiple locations needed for high quality SPECT images of heart 40 for both typical and large sized patients having different thoracic contours, weights, and different sized hearts located further from central longitudinal axis 32 than a typical patient 26.

Because the collimator subsystem 18, FIGS. 1-5, 8 and 9 is not circular, slits 52, 52a are not evenly spaced angularly with respect to the center of PIV 42, FIG. 2, PIV 42a, FIG. 3, or PIV 42b, FIG. 8. This unevenness in angular sampling requires computer subsystem 25, FIG. 1 to utilize iterative algorithms, such as Ordered Subset-Expectation Maximization (OS-EM), for tomographic image reconstruction.

Collimator subsystem 18, FIGS. 1-5, 8 and 9 preferably includes a plurality of transversely spaced slats 54, as shown in FIGS. 4 and 5, disposed behind and physically separate from the slit-plate 30. Slats 54 longitudinally collimate the radiation photons. In one example, the distance between each of the plurality of transversely spaced slats 54 is configured to adjust spatial resolution of longitudinal collimation. Slats 54 are typically multiple thin parallel lead plates or foils, and may be separated with Styrofoam plates (not shown) of uniform thickness, e.g., about 2-5 mm. Slats 54 basically fill the space (with varied radial length, e.g., 50-100 mm), between the two ends of collimator subsystem 18 and between collimator subsystem 18 and detector subsystem 20.

Figure 10:
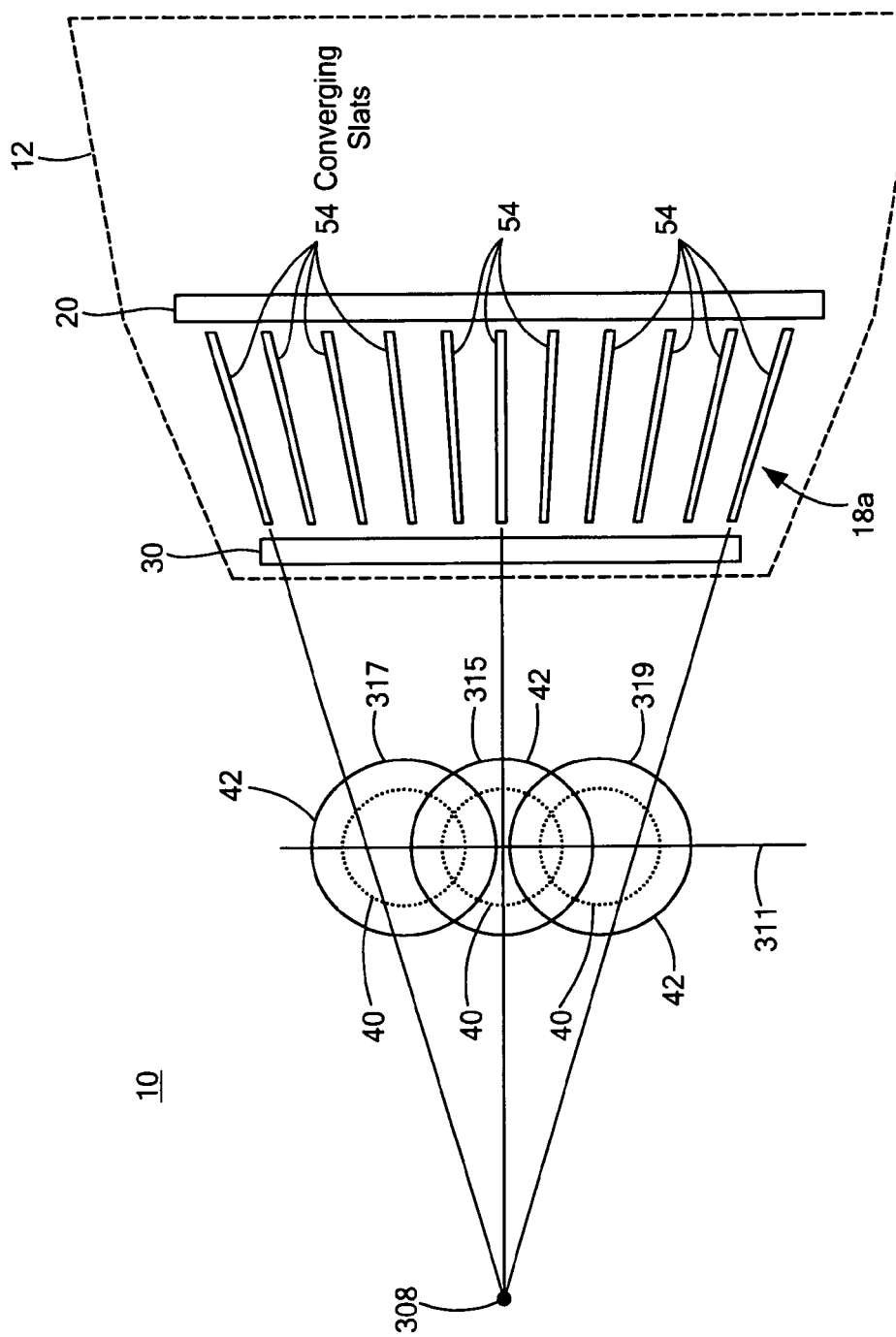
FIG. 10 is a schematic side view of one embodiment of the SPECT system for cardiac imaging having a collimator subsystem with converging slats.

In one embodiment, SPECT system 10, FIG. 10, shown in a longitudinal plane, includes collimator subsystem 18a having a plurality of transversely-spaced slats 54 which converge on predetermined focal points, shown in two dimensions as point 308. In this embodiment, collimator subsystem 18a of system 10 utilizes a variation of conventional cone-beam geometry (which relies on a collimator design with a plurality of pin holes which are all aligned in three-dimension to a single point beyond the target organ, such as the brain) for each slit of collimator subsystem 18, e.g., slits 52, FIGS. 2-3, for PIV 42, 42a, respectively. The advantage of using converging-slats 54 is the increased solid angle for photon detection, and corresponding increased geometric sensitivity. Appropriate cone-beam algorithms are applied in image reconstruction. However, since cone-beam sampling may have limitations in providing artifact-free 3D images, mainly in the upper and lower regions of the cone-beam, a few additional longitudinal sampling could be utilized to reduce these artifacts and provide satisfactory images. In this example, patient positioning subsystem, FIG. 1, moves patient 26 up and down along longitudinal axis 311 to acquire more cone-beam data sets from the radiation photons emitted from heart 40 encompassed by PIV 42 in the longitudinal plane. In this example, PIV 42 (or PIV 42a, FIG. 3) encompassing heart 40 is sampled three times at positions 317, 315, and 319. Using converging-slats 54 increases the solid angle of radiation photons received by detector subsystem 20 and increases detection efficiency by detector subsystem 20. The result is high speed or high quality SPECT imaging of heart 40.

Figure 11:
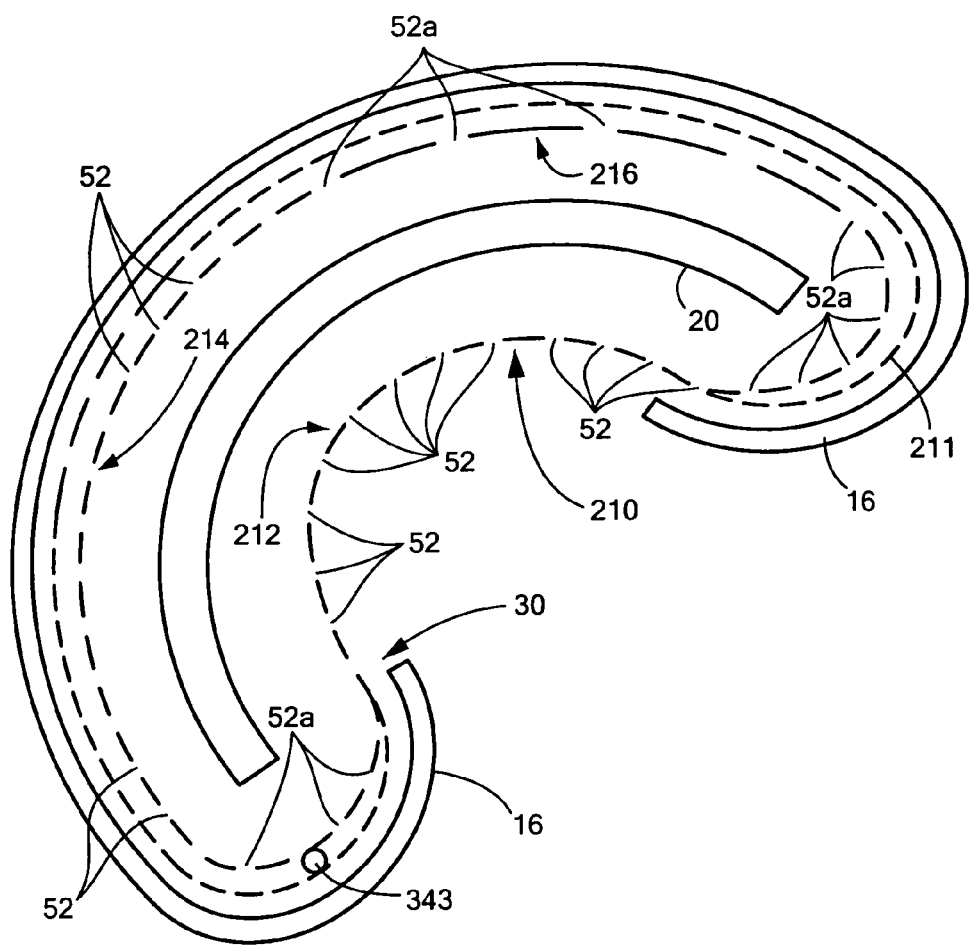
FIG. 11 is a schematic top view of one embodiment of the SPECT system for cardiac imaging of this invention including a movable loop having a plurality of sections for defining multiple PIVs.

In one preferred design, slit-plate 30, FIGS. 2-5, 8 and 9 is configured as movable loop 210, FIG. 11. Loop 210 is slideably coupled to frame 16. Movable loop 210 includes a plurality of sections, e.g., section 212, section 214, and section 216. Each of sections 212, 214 and 216 include a predefined number of spaced longitudinal slits 52, 52a, each having slit-guides 56 proximate each side thereof at a predetermine angle and each having a predetermined width to define PIV 42, FIG. 2, PIV 42a, FIG. 3, and PIV 42b, FIG. 8, respectively, as discussed above. In this example, section 212 is shown located at the front of collimator subsystem 18.

Figure 12:
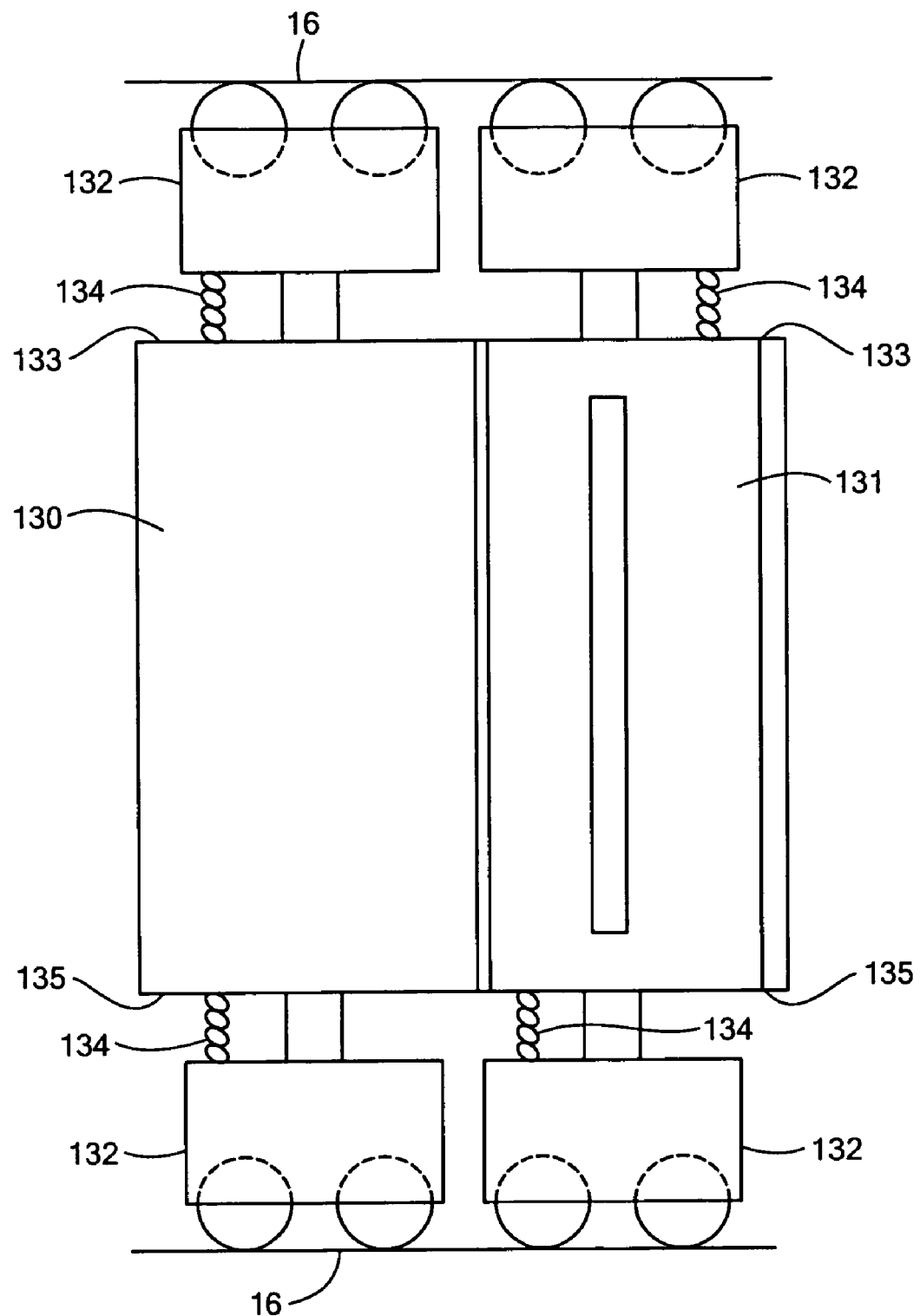
FIG. 12 is a schematic front view showing one example in detail the two collimator segments in a collimator section shown in FIG. 11.
Figure 13:
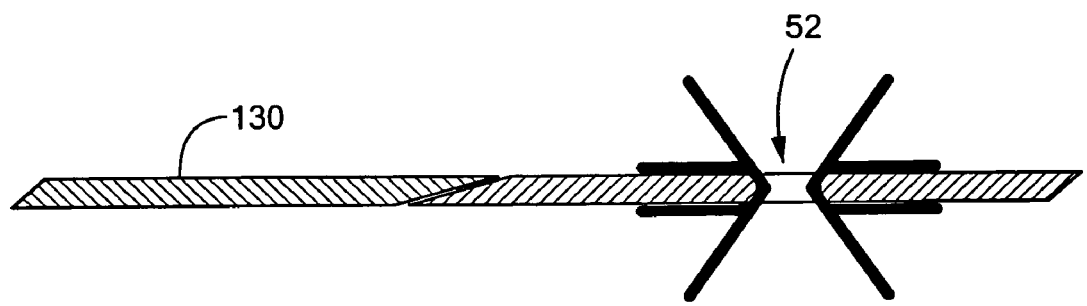
FIG. 13 is a schematic top view showing in further detail the structure of the segments shown in FIG. 12.

Each of sections 212-216 of each section is preferably coupled to movable cars 132, FIG. 12. For example, section 212 includes a plurality of segments 130 and 131, as shown in greater detail in FIG. 13, which are coupled on top surface 133, FIG. 12 to cars 132 movably coupled to frame 16 and coupled on bottom surface 135 to movable cars 132 coupled the frame 16. In one design, biasing devices 134, e.g., springs, disposed between cars 132 and segments 130 and 131 maintains segments 130 and 131 in an appropriate and reproducible position for imaging. In an exemplary embodiment, stepper-motor 343, FIG. 11, controlled by computer subsystem 25, FIG. 1 drives cars 132, FIG. 12 on tracks (not shown) in frame 16 so that the desired section of loop 210, FIG. 11, is located at the front of collimator subsystem 18 for imaging.

In one design, collimator subsystem 18, FIG. 11 includes a plurality of connected loops, e.g., loop 210 and loop 211 that each including a plurality of sections and share a common section, e.g., section 210 disposed proximate patient 26. As discussed above, each of the connected loops 210 and 211 are slideably coupled to frame 16. A switching system may be used to select the track of choice and allow a specific section to be pulled to the front. The track flexibilities and functionalities are available from well-developed track technology.

The result is SPECT system 10 for cardiac imaging, FIGS. 1-13 of this invention, can select a desired PIV 42, FIG. 2, PIV 42a, FIG. 3, or PIV 42b, FIG. 8, as needed for different sized patients and for scout imaging by simply moving the desired section 212-214, FIG. 11, to the front of collimator subsystem 18 to provide scout images and high quality SPECT images of the heart.

In one embodiment of this invention, the distance, d, indicated at 44, FIGS. 2 and 3, between slit-plate 30 of collimator subsystem 18 and detector subsystem 20 is configured for minification of the plurality of simultaneous non-overlapping projections 200, 200a on the detector subsystem 20. To accommodate the large number of plurality of projections 200, 200a, on detector subsystem 20, each projection needs to be small enough so that there is no overlap of adjacent projections, 200, 200a and a maximum number of projections can be accommodated on detector subsystem 20. This is achieved through minification of the plurality of projections 200, 200a by adjusting distance d-44 at the appropriately the distance between the slit-plate 30 and detector subsystem 20, e.g., to a distance of about 5-10 cm and by adjusting the angle of plurality of slit-guides 56, FIGS. 6 and 7, e.g. $\theta_1$-55 and $\theta_2$-57 with respect to axis 59. The angle of slit-guides 56 limits the radiation photons only from PIV 42, FIG. 2, or PIV 42a, FIG. 3. This design allows a large number of non-overlapping projections of a finite-sized PIV to be acquired simultaneously and thus provides high geometric efficiency in detection of the radiation photons emitted from PIV 42 or PIV 42a, used or SPECT imaging of heart 40.

In one design of this invention, patient positioning subsystem 12, FIG. 1, positions patient 26 to one or more predetermined locations defined by PIV 42, FIG. 2, PIV 42a, FIG. 3, or PIV 42b, FIG. 8, so that patient 26 can be rotated on a central axis of the appropriate PIV which contains the heart 40 throughout the whole series of rotation for SPECT imaging (discussed in detail below). Patient positioning subsystem 12, FIG. 1, may include chair 13 that is incrementally rotated to obtain a plurality of projection images. The longitudinal axis of the frame 16 may be oriented nearly, but not exactly, vertically such that the patient 26 sits nearly upright. More realistically, patient 26 should sit in a slightly reclined bucket seat, with his back firmly supported so that patient 26 feels comfortable, with low likelihood of torso movement, to go through the imaging procedure. This arrangement facilitates rotation of patient 26 during imaging and allows a small footprint of the system 10. Upright imaging provides the advantage of lowering the diaphragm of the patient 26, thus reducing the severity of attenuation and scatter effects caused by sub-diaphragmatic organs and sub-diaphragmatic tracer accumulations.

Patient positioning subsystem 12, FIG. 1, positions patient 26 so that the center of the heart 40 is at center 32, FIGS. 2 and 3, of the three-dimensional field PIV 42 or PIV 42a based on a previous scout imaging of the heart. However, a single set of plurality of 12-20 projections is typically not enough for reconstructing high quality SPECT images of heart 40. Thus, several (2-5) additional sets of non-redundant projections may be acquired, depending on image quality requirements of the specific clinical application. These additional sets of non-redundant projections can be added by rotating patient 26 on the positioning subsystem 12, FIG. 1, relative to the other hardware, to sample slightly different projections. Patient positioning subsystem 12, then incrementally rotates patient 26, e.g., approximately 3° for a total of 12° to 15° to fill in the angular sampling gaps about a predefined central longitudinal axis, e.g., center 32 of PIV 42, FIG. 2 or center 32, FIG. 3 of PIV 42a, and then intermittently remains stationary, e.g., for about 30-120 seconds to obtain additional plurality of ECT projections 200, FIG. 2 or a plurality of projections 200a, FIG. 3. Frame 16, collimator subsystem 18 and detector subsystem 20 remain stationary at all times. Computer subsystem 25, FIG. 1, reconstructs SPECT images from the whole sets of the plurality of ECT projections 200, FIG. 2, or the plurality of projections 200a, FIG. 3.

In one exemplary operation of SPECT system 10, FIGS. 1-13 of this invention, patient set-up and imaging proceeds as follows. After patient 26, FIG. 1 is secured in chair 13 of patient position subsystem 12 with body restraints, patient 26 and chair 13 are first moved to a default position for scout-imaging, e.g., PIV 42b, FIG. 8, in the frame 16. Electronic control of the system 10 is provided by computer system 25, FIG. 1, having a monitor (not shown) for data visualization, as is known to those skilled in the art. Section 216, FIG. 11, with wider slits 52a on loop 210, e.g., as shown in greater detail in FIG. 5, is already in the front of collimator subsystem 18. Scout SPECT imaging of a large PIV 42b, FIG. 8, covering the lower thorax is immediately performed with the collimator subsystem 18. In about 30 seconds, three low-resolution real-time reconstructed SPECT images show up on the monitor for the three standard orthogonal slices across the center of the heart. The location of the heart 40 gradually becomes clear on all three slices as a distinct blurry disk. The operator may then be prompted to verify the computer identified three-dimensional center and the general size of the heart 40, as indicated on the monitor with a 10 cm or a 14 cm circles as best-matched reference, the outline of a three-dimensional sphere superimposed on each of the three slices.

Approximately 1-2 minutes into acquisition, as the displayed three-dimension scout-SPECT images gain more statistics to confirm the match, the operator clicks a software control button to approve the center location of the sphere, the displacement necessary to bring the heart into an appropriate PIV is determined. At the same time, a decision of which PIV, e.g., PIV 42a, FIG. 2, or PIV 42b, FIG. 3, will be selected for imaging is also determined and confirmed based on the displayed size of the heart.

Following the necessary translations, patient position subsystem 12, FIG. 1, moves patient 26 in three-dimensions to center the heart 40 at the center 32, FIG. 2 of PIV 42, or PIV 42a, FIG. 3 and locks in place. At the same time, section 212, FIG. 11, with PIV 42 on loop 210, or section 214 with PIV 42a on loop 210, for a larger patient 26, or for a larger heart, is moved to the front of collimator subsystem 18. As soon as the patient motion stops and the appropriate collimator subsystem 18, FIGS. 2 and 3, is properly configured, core SPECT imaging of heart 40 begins with a large number of projections acquired from multiple directions simultaneously for 0.5 to 2 minutes. In an alternative embodiment, scout imaging may be performed using acquired raw projections to determine the 3D center and the size of the heart without SPECT image reconstruction.

When acquiring high-resolution core SPECT images of heart 40, the required rotation of patient is a small angle rotation utilizing only several additional (2-5) steps. Patient positioning subsystem 13 rotates patient 26, for example, about 3° per step for a total of 15° in five additional steps. Thus, for a collimator system as shown in FIGS. 2-4, a total of 72 to 78 projections may be acquired in 3 to 12 minutes.

The result is system 10, FIGS. 1-14, is capable of achieving high performance either in high spatial or high temporal resolution and has significant advantages over the current state-of-the-art SPECT systems. These advantages include, inter alia, high quality SPECT images of the heart, achieved through accurate, optimal and reproducible positioning guided by scout imaging, increased overall detector utilization and detection efficiency, inherent detector stability, mechanical simplicity, the ability to define multiple PIVs to accommodate both typical and larger patients which accommodates the majority of patients of a patient population, compact physical size, predictable and reproducible system and imaging performance, simple, practical, standardized and automated clinical operations. Further, the small footprint of the system meets the need of hospitals and physician offices to reach a large patient population.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A single photon emission computed tomography (SPECT) system for cardiac imaging comprising:
    a stationary open arc-shaped frame;
    a stationary open arc-shaped collimator subsystem for optimizing collimation of radiation photons emitted from the heart, the collimator subsystem configured to: approximately match the shape of the thoracic contour of patients having different sizes and weights, locate the collimator subsystem closely proximate a heart of a patient and define a plurality of predetermined image volumes each having a central longitudinal axis, each of the plurality of predetermined imaging volumes configured to encompass the heart of patients of different sizes and weights;
    a stationary open arc-shaped detector subsystem proximate the collimator subsystem and having a shape generally matching the shape of the collimator subsystem configured to detect collimated radiation photons from the collimator subsystem and generating output electrical signals for the generation of one or more SPECT images and;
    a computer subsystem configured to receive the digitized output electrical signals from the detector subsystem and generate a plurality of SPECT images of the heart.

2. The system of claim 1 in which the shape of the collimator subsystem and the detector subsystems optimize collimation and detection of the radiation photons for a majority of the patients of a patient population.

3. The system of claim 1 in which each of the plurality of predetermined imaging volumes includes a three-dimensional cylindrical imaging volume.

4. The system of claim 1 in which the arc-shaped frame, the arc-shaped collimator subsystem, and the arc-shaped detector subsystem are subtended at an angle in the range of about 180° to 220° with respect to the center of the predetermined imaging volume.

5. The system of claim 1 in which the collimator subsystem includes a slit-plate comprising a predetermined number of spaced longitudinal slits each having a predetermined width for transversely collimating the radiation photons.

6. The system of claim 5 in which the predetermined width of each of the plurality of spaced longitudinal slits is configured to adjust spatial resolution of transverse collimation.

7. The system of claim 6 further including a plurality of slit-guides attached proximate each side of each of the plurality of longitudinal slits.

8. The system of claim 7 in which the angle of the slit-guides and the location of the spaced longitudinal slits in a transverse plane are configured to provide a plurality of non-overlapping projections that define the size and location of the plurality of predetermined imaging volumes.

9. The system of claim 8 in which the size and location of each of the plurality of predetermined image volumes and the plurality of non-overlapping projections provides high geometric efficiency in the detection of radiation photons emitted from the heart.

10. The system of claim 8 in which each of the plurality of predetermined imaging volumes are configured for patients having different thoracic contours and/or different sized hearts and/or different locations of the heart relative to a predefined central axis.

11. The system of claim 8 in which the plurality of predetermined imaging volumes include a large three-dimensional imaging volume for generating a scout image which estimates a three-dimensional center and the size of the heart.

12. The system of claim 8 in which the plurality of predetermined imaging volumes include a small three-dimensional imaging volume for generating SPECT images of the heart.

13. The system of claim 12 in which the combination of the location of spaced longitudinal slits, the angle of the slit-guides, and the distance between the slit plate and the detector subsystem are adjusted for minification of a plurality of simultaneous non-overlapping projections such that a maximum number of projections can be cast on the detection system to provide high geometric efficiency for generating one or more SPECT images.

14. The system of claim 13 in which the one or more SPECT images are obtained by using image reconstruction of the plurality of simultaneous non-overlapping projections.

15. The system of claim 8 in which the collimator subsystem includes a plurality of longitudinally spaced transversely oriented slats disposed behind the slit-plate for longitudinally collimating the radiation photons.

16. The system of claim 15 in which the location of each of the plurality of longitudinally spaced transversely oriented slats is configured to adjust spatial resolution of longitudinal collimation.

17. The system of claim 16 in which the longitudinally spaced transversely oriented slats are configured to converge on predetermined focal points to accommodate cone-beams of radiation photons emitted from the heart for increasing the number of radiation photons detected by the detector subsystem.

18. The system of claim 8 in which the slit-plate is configured as a flexible loop moveably coupled to the frame having a plurality of sections each configured to provide a unique predetermined imaging volume having a predetermined size and location, and a spatial resolution.

19. The system of claim 18 in which a desired section of the flexible loop is positioned proximate and surrounding one of the plurality of predetermined imaging volumes of the patient by driving the flexible loop to a predetermined location on the collimator subsystem.

20. The system of claim 19 further including a plurality of connected flexible loops moveably coupled to the frame, each loop including a plurality of sections configured to provide a unique predetermined imaging volume of a predetermined size, location, and spatial resolution.

21. The system of claim 1 further including a patient positioning subsystem configured to position the patient about the central longitudinal axis of a predetermined imaging volume selected from the plurality of imaging volumes such that the heart is located proximate the center of the selected predetermined imaging volume.

22. The system of claim 21 in which the patient positioning subsystem incrementally rotates the patient about the central longitudinal axis of the selected imaging volume to obtain a plurality of additional projection images.

23. The system of claim 22 in which the patient positioning subsystem intermittently and incrementally rotates the patient about a predefined central longitudinal axis of a small predetermined three-dimensional imaging volume for obtaining a plurality of sequentially acquired sets of simultaneous projections and reconstructing one or more SPECT images.

24. The system of claim 21 in which a patient positioning subsystem positions a predetermined imaging volume encompassing the heart up and down about a longitudinal axis for acquiring additional cone-beam data set in a longitudinal plane.

25. The system of claim 1 in which the open arc-shaped frame has a shape closely matching the shape of the collimator subsystem.

26. A single photon emission computed tomography (SPECT) system for cardiac imaging comprising:
    a stationary open arc-shaped frame;
    a stationary open arc-shaped collimator subsystem for optimizing collimation of radiation photons emitted from the heart, the collimator subsystem configured to: approximately match the shape of the thoracic contour of patients having different sizes and weights, locate the collimator subsystem closely proximate a heart of a patient and define the plurality of predetermined image volumes each having a central longitudinal axis, each of the plurality of predetermined imaging volumes configured to encompass the heart of patients of different sizes and weights;
    a stationary open arc-shaped detector subsystem proximate the collimator subsystem and having a shape generally matching the shape of the collimator subsystem configured to detect collimated radiation photons from the collimator subsystem and generating output electrical signals for the generation of one or more SPECT images and;
    a patient positioning subsystem configured to position the patient about the central longitudinal of a predetermined imaging volume selected from the plurality of imaging volumes such that the heart is located proximate the center of the selected predetermined imaging volume.

27. A single photon emission computed tomography (SPECT) system for cardiac imaging comprising:
    an open arc-shaped frame;
    a collimator subsystem shaped to approximately match the thoracic contour of patients having different sizes and weights and shaped to surround and position the collimator subsystem closely proximate a heart of a patient of said patients encompassed by at least one predetermined image volume configured for optimizing collimation of radiation photons emitted from the heart, the collimator system further including a slit-plate configured as a flexible loop moveably coupled to the frame having a plurality of sections each configured to provide a unique predetermined imaging volume having a predetermined size and location, and a spatial resolution; and
    an open arc-shaped detector system coupled to the collimator subsystem having a shape closely matching the shape of the collimator subsystem for detecting collimated radiation photons from the collimator subsystem and generating output electrical signals.

* * * * *